(12) United States Patent
Erickson et al.

(10) Patent No.: US 9,750,573 B2
(45) Date of Patent: *Sep. 5, 2017

(54) SHARPS CONTAINER (71) Applicant: ULTIMED, INC., Excelsior, MN (US)

(72) Inventors: Thomas E. Erickson, Crosslake, MN (US); James J. Erickson, Mound, MN (US); Thomas Sauro, Rosemount, MN (US)

(73) Assignee: ULTIMED, INC., Excelsior, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/579,379

(22) Filed: Dec. 22, 2014

(65) Prior Publication Data

US 2015/0108021 A1  Apr. 23, 2015

Related U.S. Application Data

(63) Continuation of application No. 12/247,684, filed on Oct. 8, 2008, now Pat. No. 8,915,362.

(51) Int. Cl.
| | |
|---|---|
| *B65D 25/04* | (2006.01) |
| *A61B 19/02* | (2006.01) |
| *A61M 5/32* | (2006.01) |
| *A61M 5/00* | (2006.01) |
| *A61B 50/00* | (2016.01) |
| *A61B 50/30* | (2016.01) |
| *A61B 50/36* | (2016.01) |

(52) U.S. Cl.
CPC ...... *A61B 19/0262* (2013.01); *A61B 50/3001* (2016.02); *A61B 50/362* (2016.02); *A61M 5/002* (2013.01); *A61M 5/3205* (2013.01); *A61B 2050/0057* (2016.02); *A61B 2050/3004* (2016.02); *A61B 2050/3008* (2016.02); *A61B 2050/364* (2016.02)

(58) Field of Classification Search
CPC . A61M 5/002; A61M 5/3205; A61B 19/0262; A61B 19/0288
USPC .................. 220/502, 529; 206/366
See application file for complete search history.

(56) References Cited

U.S. PATENT DOCUMENTS

| | | | |
|---|---|---|---|
| 4,862,573 A | 9/1989 | Kelson et al. | |
| 4,890,733 A | 1/1990 | Anderson | |
| 5,046,614 A | 9/1991 | Torres et al. | |
| 5,065,939 A | 11/1991 | Boothe et al. | |
| 5,097,950 A | 3/1992 | Weiss et al. | |
| 5,127,522 A | 7/1992 | Ranford | |

(Continued)

FOREIGN PATENT DOCUMENTS

| | | |
|---|---|---|
| WO | 2005120510 A2 | 12/2005 |
| WO | 2005120611 A2 | 12/2005 |
| WO | 2009117505 A1 | 9/2009 |

*Primary Examiner* — King M Chu
(74) *Attorney, Agent, or Firm* — Seager, Tufte & Wickhem LLP (57) ABSTRACT

The disclosure relates to a multifunctional sharps container having a first dispensing compartment for storing unused sharps and a second compartment for receiving used sharps. The first and second compartments are separated by a generally liquid impermeable partition fixed to the walls of the container. In addition, the first and second compartments are provided with apertures and structures for conveying the sharps, out of and into the compartments respectively, which are functional in at least two orientations of the container.

20 Claims, 9 Drawing Sheets

(56) References Cited

U.S. PATENT DOCUMENTS

| | | | |
|---|---|---|---|
| 5,152,394 A | 10/1992 | Hughes | |
| 5,190,185 A | 3/1993 | Blechl | |
| 5,240,108 A | 8/1993 | Tonna | |
| 5,245,117 A * | 9/1993 | Withers et al. | 588/249 |
| 5,344,007 A * | 9/1994 | Nakamura et al. | 206/205 |
| 5,409,113 A | 4/1995 | Richardson et al. | |
| 5,413,243 A | 5/1995 | Bemis et al. | |
| 5,494,158 A | 2/1996 | Erickson | |
| 5,545,145 A | 8/1996 | Clinton et al. | |
| 5,573,113 A | 11/1996 | Shillington et al. | |
| 5,603,404 A | 2/1997 | Nazare et al. | |
| 5,626,230 A * | 5/1997 | Shanley et al. | 206/571 |
| 5,806,668 A * | 9/1998 | Bixby | A41D 19/0068 15/227 |
| 6,053,314 A | 4/2000 | Pittman | |
| 6,283,909 B1 | 9/2001 | Sharp | |
| 6,685,017 B2 * | 2/2004 | Erickson | 206/366 |
| 6,745,898 B2 | 6/2004 | Lin | |
| 6,769,362 B2 | 8/2004 | Okubo et al. | |
| 6,792,662 B2 * | 9/2004 | Samuel | 29/426.5 |
| 6,923,318 B1 * | 8/2005 | Erickson et al. | 206/366 |
| 6,923,319 B1 | 8/2005 | Erickson et al. | |
| 7,344,027 B2 | 3/2008 | Erickson et al. | |
| 7,513,363 B2 * | 4/2009 | Brown | A61M 5/3205 206/366 |
| 7,556,149 B2 * | 7/2009 | Erickson et al. | 206/366 |
| 7,815,046 B2 * | 10/2010 | Sansoucy et al. | 206/366 |
| 2001/0019024 A1 * | 9/2001 | Boyd-Moss | B65D 81/264 206/363 |
| 2002/0151952 A1 * | 10/2002 | Perouse | 623/1.11 |
| 2002/0182102 A1 | 12/2002 | Fontenot et al. | |
| 2003/0029014 A1 | 2/2003 | Samuel | |
| 2003/0040715 A1 | 2/2003 | D'Antonio et al. | |
| 2003/0132129 A1 | 7/2003 | Erickson | |
| 2005/0269227 A1 * | 12/2005 | Erickson | A61M 5/3205 206/366 |
| 2005/0269320 A1 | 12/2005 | Erickson et al. | |
| 2006/0032769 A1 | 2/2006 | Erickson et al. | |
| 2006/0243619 A1 * | 11/2006 | Brown | A61M 5/3205 206/366 |
| 2006/0243635 A1 | 11/2006 | Sullivan et al. | |
| 2008/0135434 A1 | 6/2008 | Erickson et al. | |

* cited by examiner

SHARPS CONTAINER

RELATED APPLICATIONS

This application is a continuation of U.S. application Ser. No. 12/247,684, filed Oct. 8, 2008, now U.S. Pat. No. 8,925,362.

BACKGROUND OF THE INVENTION

A world-wide health care problem and need is the disposal of used syringes; this is a continuing health threat to the public. Of great concern, of course, are AIDS and other serious infectious diseases such as hepatitis. And, needles can become contaminated when used to treat various conditions such as allergies, infertility, arthritis, migraines, HIV, growth hormones among others.

Health care regulations have mandated the safe disposal of used syringes. A number of approaches, procedures and apparatus have been proposed for the storage of used syringes and the subsequent disposal thereof.

After a needle has been used either by or on a patient, then the syringe needle is contaminated from contact with the blood of the patient. If the user is HIV positive or a carrier of hepatitis or other blood born pathogen, then an accidental needle stick by the contaminated needle could spread the disease.

In hospitals and clinics the health care industry uses special containers dedicated for the disposal of needles and other invasive devices. Such containers are frequently referred to as "sharps" containers. The sharps containers with used syringes/needles therein are then disposed by industrial waste collectors and are usually either burned, disintegrated or buried, depending upon local health care regulations.

There is an additional dimension to the problem; that is the uses of syringes in private homes. For example, home syringe users are frequently diabetics who require frequent doses of insulin to regulate their glucose level. The practice of disposing and safe storage of used syringe syringes in private homes is far less organized than in hospitals and clinics. Home disposing techniques are varied and frequently home invented, using discarded or empty containers found around the home; such arrangements are high risk for accidental spreading of disease. There is currently no standard disposal practice for insulin users.

Medical delivery pens have become widely used in place of, or in addition to, medical syringes, e.g., by diabetics, who frequently inject themselves several times a day with accurately measured, adjustable, pre-selected amounts of insulin or other medication. Medical delivery pens include a reservoir of medication and a distal end adapted to be attached, usually by thread means, to a pen needle assembly. As is well known (see, for example, FIG. 1 of U.S. Pat. No. 5,545,145), a pen needle assembly has, within an outer, generally cylindrical shield, a generally cylindrical housing within which is mounted an axially extending hollow needle, (i) the proximal end of which punctures a seal in the distal end of the medical delivery pen to allow the flow there-through of medication when the delivery pen is screwed into the proximal end of the pen needle cylindrical housing, and (ii) the distal end of which is for insertion into tissue of the person requiring the medication. The pen needle assemblies typically also include a removable thin sterile seal covering the proximal (large diameter) end of the outer shield and a removable tube-like shield covering the distal portion of the hollow needle. The pen needle assembly is then factory sterilized. The user of a pen needle assembly removes the seal from the outer shield, screws the pen into the proximal end of the pen needle housing, removes the outer and tube-like shields, sets the medical delivery pen for the desired dose of medication, and then inserts the distal end of the pen needle into the target tissue following which the medical delivery pen is actuated to deliver the desired dose of medication through the hollow needle into said tissue.

Many diabetics routinely administer medication to themselves several times a day by injection of a pre-selected quantity of insulin (or substitute medication) in liquid form; the correct amount of medication can be determined from prior professional medical instruction or by use of convenient portable blood analysis kits which are small, compact and provide rapid indicators of the user's blood sugar level. Some of the typical several daily injections are often done away from the diabetic's residence which has made the use of the portable, convenient medical delivery pens widespread. The aforesaid testing kits and the medical delivery pens are relatively small in size and can easily fit within a woman's purse or equivalent. A typical scenario for a diabetic at a restaurant for a meal is to first use the blood sugar testing kit to obtain an indicator of his or her blood sugar level. This information then facilitates programming or adjusting the medical delivery pen to deliver the desired quantity of medication. Then the pen with an attached pen needle (a pen needle assembly without the outer cylindrical and tube shields) is used to inject the tissue and dispense the medication. These steps require a relatively short length of time and can be done with minimum loss of privacy. Some people requiring multiple daily medicine injections use both medical syringes and medical delivery pens with pen needles.

Medical delivery pens are also widely used by doctors, nurses and other professionals in their duties. Many individuals will request that an injection be done with a pen needle rather than a syringe. The aforementioned professionals are especially mindful of possible dangers from a needle stick and the possible unwanted "sticks" that occur in the professional world.

The user, both individual and professional, of a pen needle assembly should, after the first use of a pen needle, carefully detach the used pen needle from the medical delivery pen and safely dispose said pen needle into a safe sharps container. The approved disposal procedure is insertion of the distal end of the needle into the tube-like shield (sometimes omitted) and thence the shielded needle and pen needle cylindrical housing into the outer cylindrical shield, unscrewing of the medical delivery pen from the proximal end of the pen needle cylindrical housing, and careful placement of the used pen needle assembly into a safe sharps container. Further, in the "perfect" world, the user of a medical syringe would safely dispose the used syringe into a safe sharps container.

Unfortunately, the recommended safe disposal procedures are not always followed. Used and potentially dangerous syringes, pen needles or pen needle assemblies are routinely left in unsafe places where third parties may unwittingly be "stuck" with possible dire consequences. Examples of such unsafe places are purses, the pockets on the back of aircraft seats, private and public wastebaskets, garbage receptacles, dumpsters and empty milk or other unsafe containers.

Further, the above described pen needle assembly or pen needle disposal procedure requires that the user or associate handle or hold the pen needle while the pen is unscrewed therefrom; this creates the possibility of a potentially dangerous "stick." Also, if the user or associate tries to insert the pen needle into the outer shield to form a pen needle assembly, then additional handling is again required with the possibility of a "stick".

Similar disposal considerations apply to the more traditional syringe needles which may have associated syringe needle covers.

SUMMARY OF THE DISCLOSURE

The present disclosure relates to a safe, space efficient container for storing a large number of medical or laboratory sharps; a multifunctional container which is especially useful for an individual such as a diabetic who may require several daily doses, which doses are often administered at the user's residence. It is desirable to provide a multifunctional container for safe storage of sharps which combines convenient storage and dispensing of unused sharps with safe storage of used sharps. Given the variety of use conditions which may be encountered in the home environment, it is desirable that the multifunctional container be functional in more than one orientation to better adapt to available storage locations. The multifunctional container may be provided with a first compartment sized and configured to contain a quantity of unused sharps at a first time, said sharps selected from pen needles, hypodermic needles, and syringes with attached hypodermic needles; a second compartment sized and configured to contain a similar quantity of used sharps at a second time, said sharps selected from pen needles, hypodermic needles, and syringes with attached hypodermic needles; and a liquid impermeable partition affixed to the container between the first and second compartments and along the entire perimeter of the liquid impermeable partition to prevent incidental transfer of fluid between the compartments. The first compartment may include a first aperture with an associated door, drawer, or other mechanism which may be opened to remove one or more sharp. The second compartment may be provided with a second aperture with a one-way mechanism for conveying a used sharp from the exterior of the multifunctional container to the interior of the second compartment. Given the variety of use conditions which may be encountered in the home environment, it is desirable that the multifunctional container be functional in more than one orientation to better adapt to available storage locations. That is, it may be capable of both dispensing and receiving sharps in a first position and in a second position. For example, the container may have a tall orientation which minimizes the footprint of the device on a counter and an alternate use orientation in which the container is placed on its side to fit on a shelf with a low overhead. It is desirable that the dispensing function and the disposal function should be available in each orientation.

While the invention is amenable to various modifications and alternative forms, specifics thereof have been shown by way of example in the drawings and will be described in detail. It should be understood, however, that the intention is not to limit the invention to the particular embodiments described. On the contrary, the invention is to cover all modifications, equivalents, and alternatives falling within the spirit and scope of the invention.

DETAILED DESCRIPTION

The following description should be read with reference to the drawings wherein like reference numerals indicate like elements throughout the several views. The drawings, which are not necessarily to scale, are not intended to limit the scope of the claimed invention.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

Although the multifunctional container described herein may be readily adapted to dispense any of a variety of unused sharps and to dispose of them safely after use, it will be convenient to describe aspects of the container as they relate to a specific type of sharp, so called pen needles. It will be understood that one of ordinary skill in the art would be capable of modifying the description herein to adapt the container for use with other sharps including, among others, hypodermic needles, unibody syringes having integral hypodermic needles, and the like. It will be further understood that the container may be readily adapted to dispense and/or receive more than one type of sharp should that be desired.

Figure 1A:
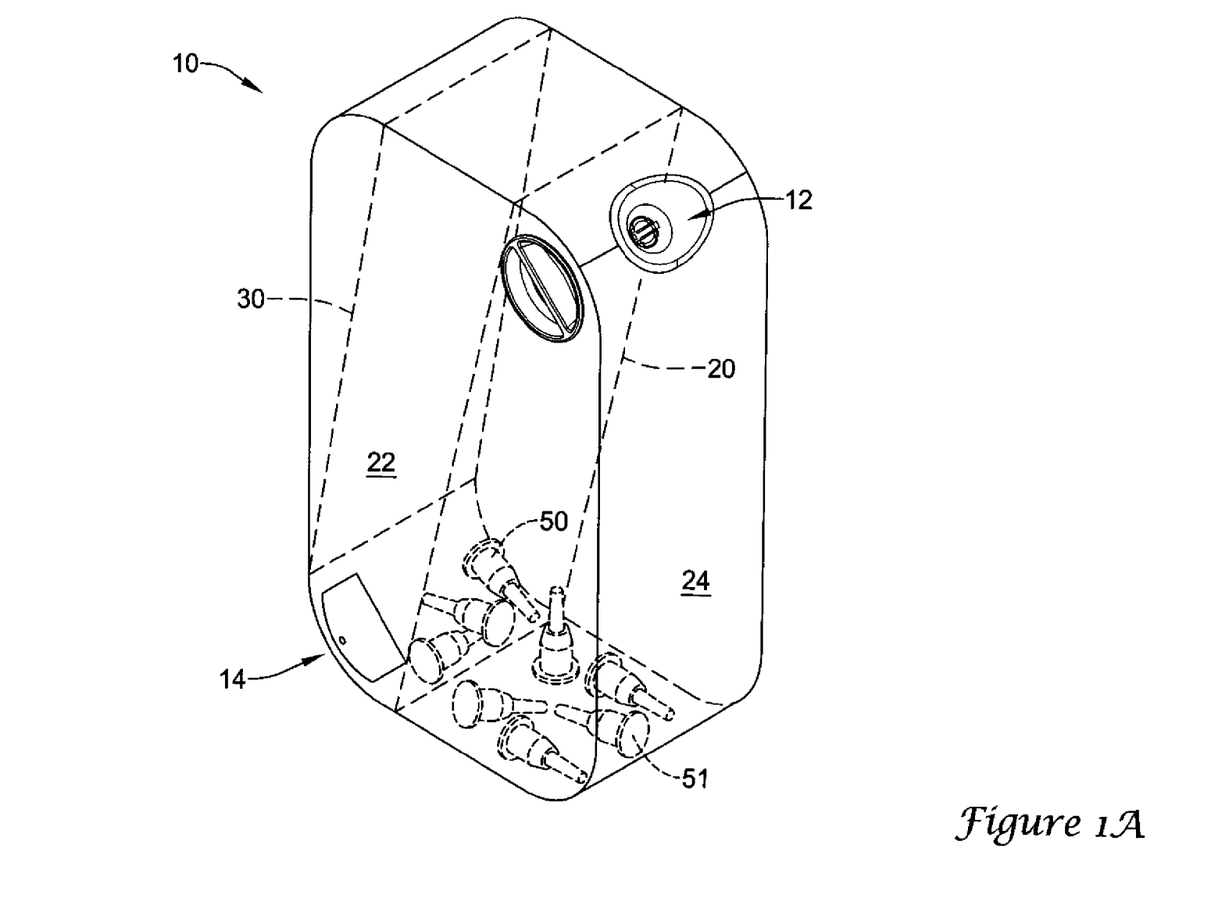
FIGS. 1A and 1B are perspective views of a multifunctional sharps container.
Figure 1B:
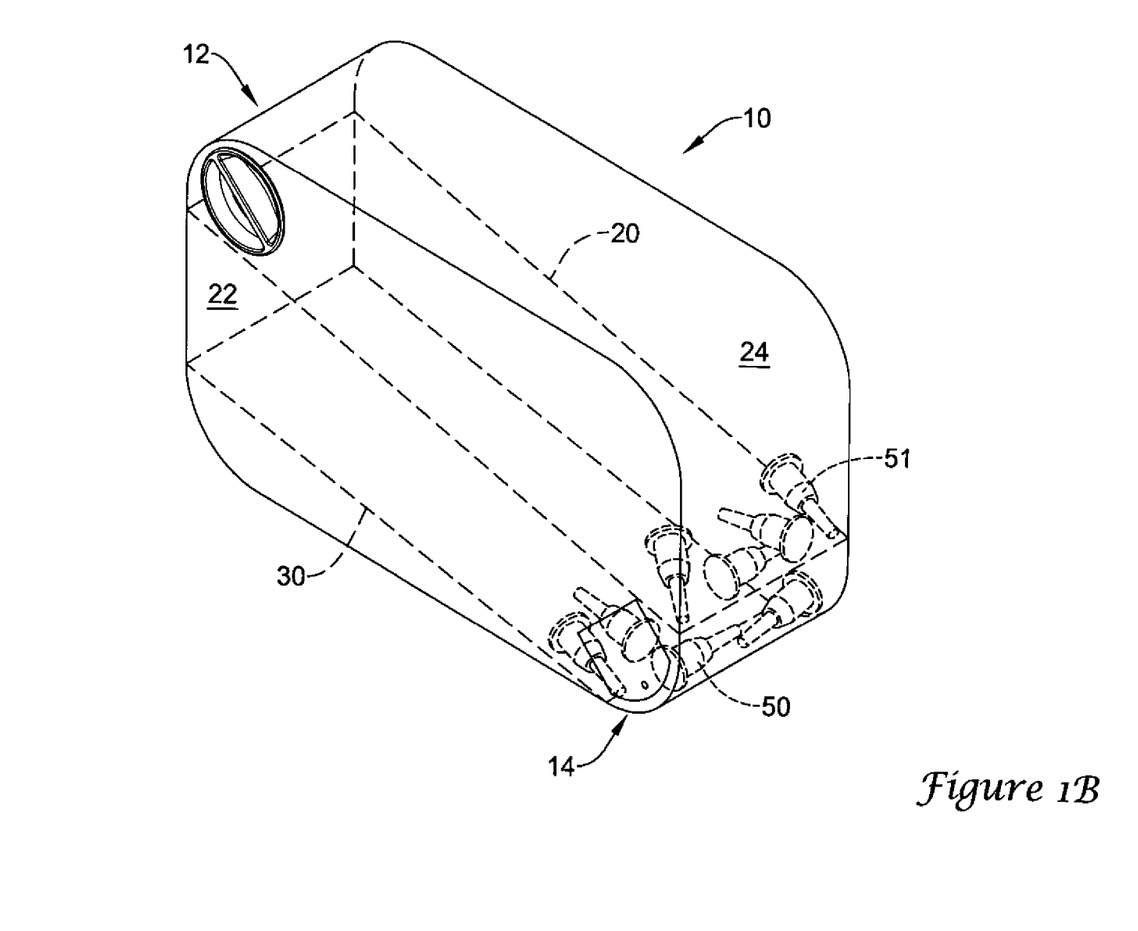

Referring now to the drawings, FIG. 1A illustrates a multifunctional sharps storage container 10 in a first functional orientation in which the longest dimension is vertical, thus providing a reduced footprint. The storage container 10 includes a first compartment 22 for storing a number of unused sharps 50 prior to use. The first compartment 22 is in communication with a first aperture 14 (shown here in schematic outline and with optional exemplary details in FIGS. 6 and 7) which may be opened to remove one or more unused sharp 50. The unused sharps may be individually packaged for removal or several sharps may be packaged together for the convenience of the user who may wish to remove, for example, a day's supply at one time. Following use, the sharp may be returned to a second compartment 24 for safe storage of a number of used sharps 51. A used sharp 51 may be introduced into compartment 24 through a second aperture 12 (shown here in schematic outline and with optional exemplary details in FIGS. 3-5). In many embodiments, aperture 12 will include a one-way component which prevents removal of used sharps 51 from the second compartment 24. It will be appreciated that FIGS. 3-5 and FIGS. 6-7 are nonlimiting representatives of suitable apertures 14 and 12 respectively. One of ordinary skill in the art will be capable of selecting aperture sizes, configurations, and features appropriate to the particular sharps to be dispensed from and to be disposed of within the multifunctional container. Although sharps 50,51 have been depicted as a pen needles enclosed in pen needle assemblies, it will be appreciated that other types of sharps may be dispensed from, and disposed of in, container 10 and that any individual sharp may, or may not, include a protective cover or container before and/or after use. The multifunctional storage container 10 includes a partition 20 separating the first compartment 22 from the second compartment 24. This partition is liquid impermeable and sealed or otherwise fixed at its perimeter to the interior walls of compartments 22 and 24 to prevent incidental transfer of liquids between the compartments, which transfer might contaminate the unused sharps 50. FIG. 1B illustrates a second functional orientation for the multifunctional container 10 of FIG. 1A in which the longest dimension is horizontal. In both the vertical and horizontal orientations, the apertures 12 and 14 remain accessible and are capable of performing their respective disposal and dispensing functions. It will be understood that the first and second orientations of the multifunctional container refer to orientations which are distinguished by which face of the container forms the base and not merely by rotation about a vertical axis. In some embodiments, the addition of surface 30 which tends to direct the sharps to be dispensed toward aperture 14 may be useful. Surface 30 may be provided as a separate element or it may result from the configuration of an appropriate wall section of the container 10. Optionally, surface 30 may be given a desired slope by the addition of legs or other structures which tilt the container as a whole when the container is disposed in a horizontal configuration.

Figure 2A:
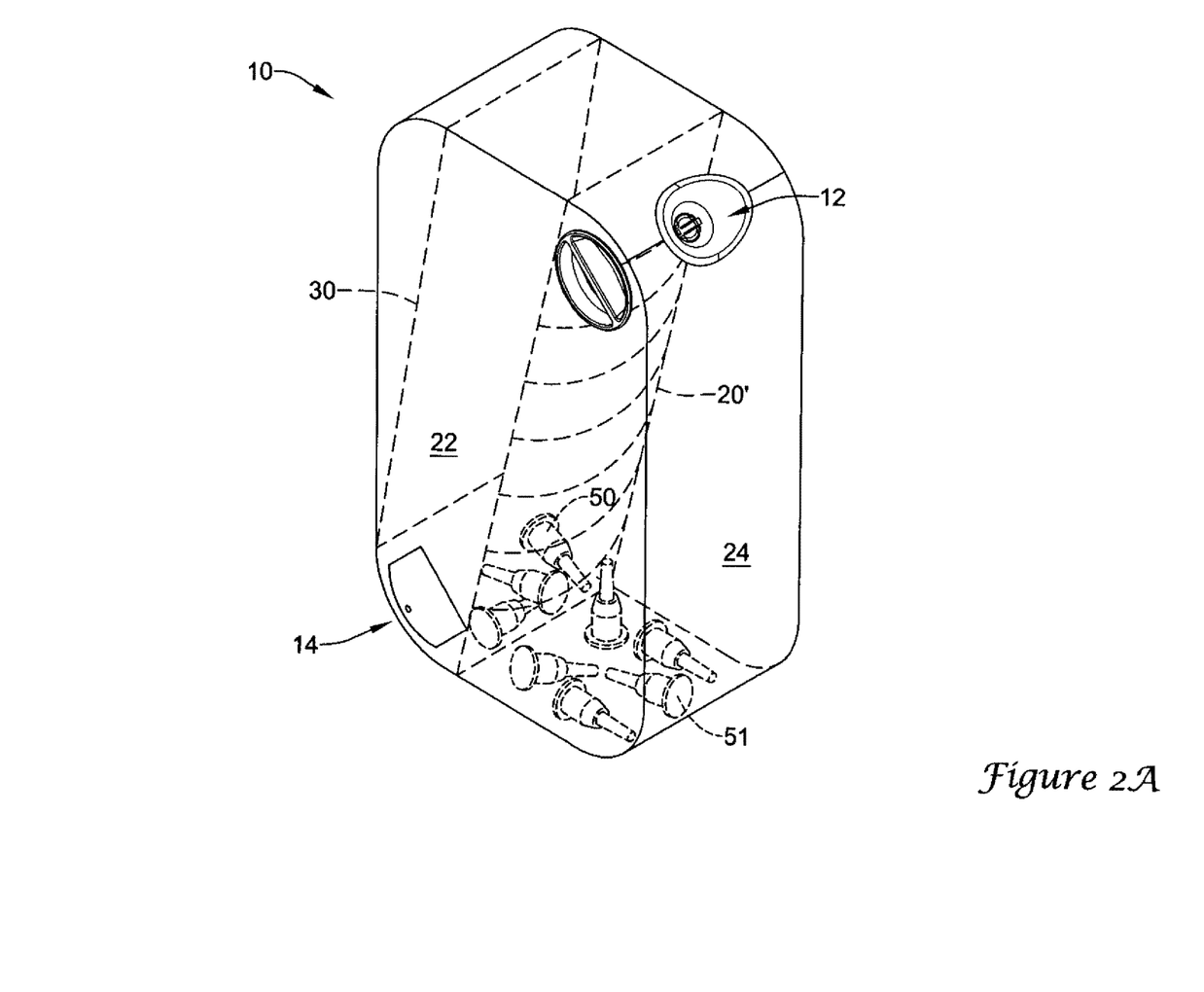
FIGS. 2A and 2B are perspective views of a multifunctional sharps container.
Figure 2B:
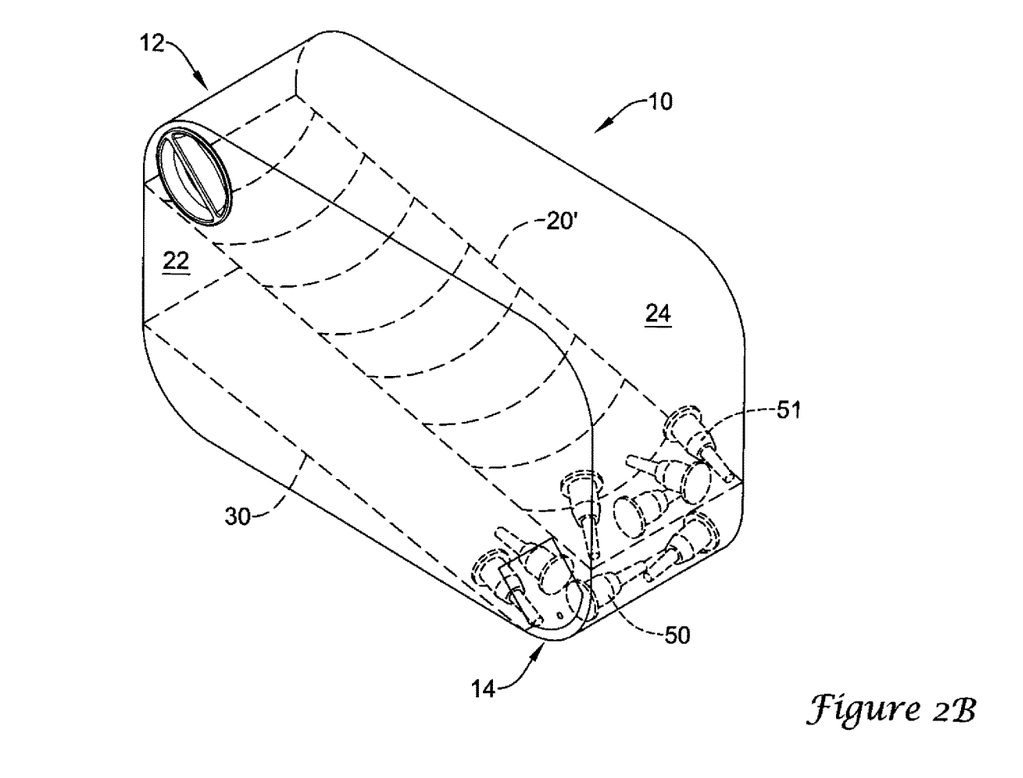

The embodiment of FIGS. 2A and 2B resembles the embodiment of FIGS. 1A and 1B except that the fixed and perimeter sealed liquid impermeable partition is flexible and is provided with sufficient extra material to allow it to deflect smoothly between positions 20A and 20B as sharps are transferred from first compartment 22 to second compartment 24. Optionally, the liquid impermeable partition is somewhat elastic and may deflect under pressure. Flexible partition 20 allows the container 10 to be smaller than would be the case if compartments 22 and 24, separated by a rigid partition 20, were both sized to hold their respective maximum quantities of sharps 50,51 throughout the useful life of the container. As before, FIGS. 3-5 and 6-7 provide several nonlimiting examples of input and output apertures 14,12 which may be employed with pen needles and pen needles assemblies. One of ordinary skill in the art will appreciate that there are other aperture related structures equally or better suited to a particular type of sharp and will select accordingly.

Figure 3:
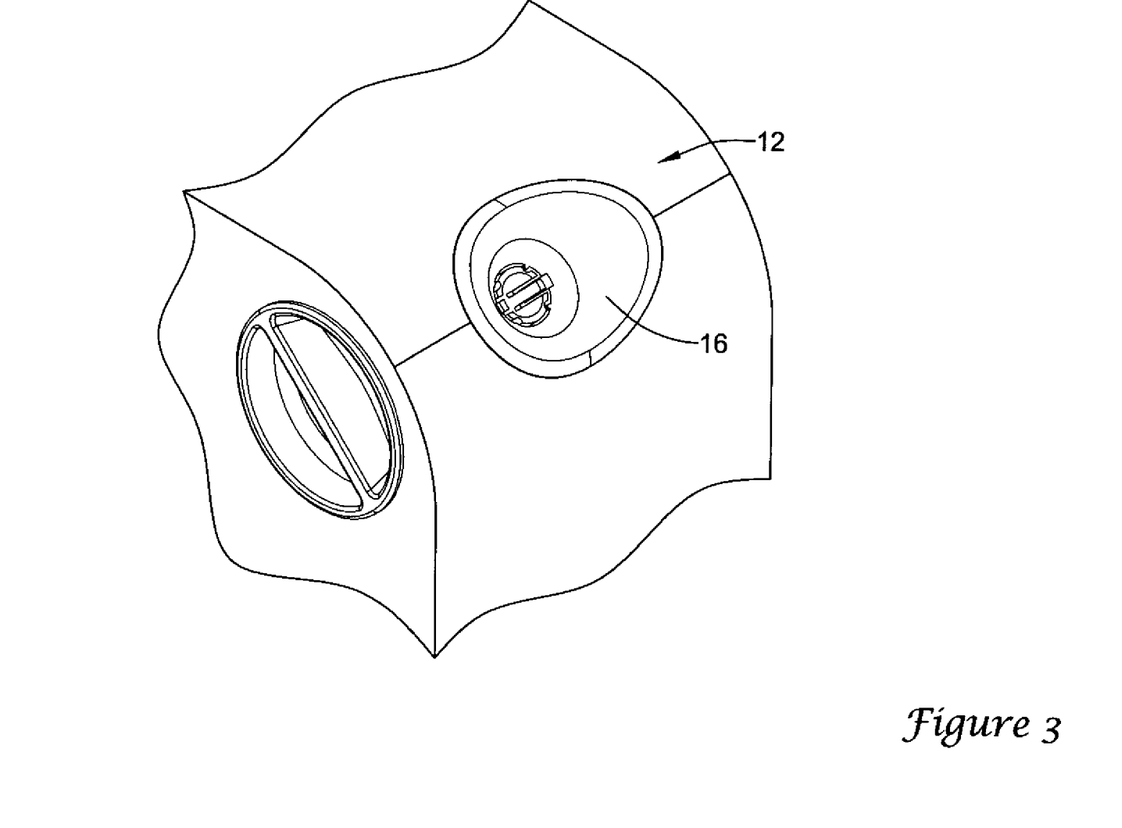
FIG. 3 is a detail including an input aperture useful in the multifunctional sharps container of either FIGS. 1A,B or 2A,B.

FIG. 3 illustrates an input aperture 12 which employs a rotary mechanism to convey a pen needle or pen needle assembly into compartment 24 of container 10. The used pen needle may be inserted into an opening in recess 16 while still attached to the delivery pen. Typically the opening will include features which mate with the pen needle, or pen needle assembly if present, to allow the delivery pen to be detached and removed in a single-handed operation. Following removal of the delivery pen or direct insertion of a detached pen needle assembly into the recess 16, the barrel may be rotated as indicated to transfer the pen needle and any associated covers or guards into compartment 24. The input aperture mechanism may include additional features such as ejectors to assist the transfer and shields to prevent the removal of a used sharp 51 from the container.

Figure 4:
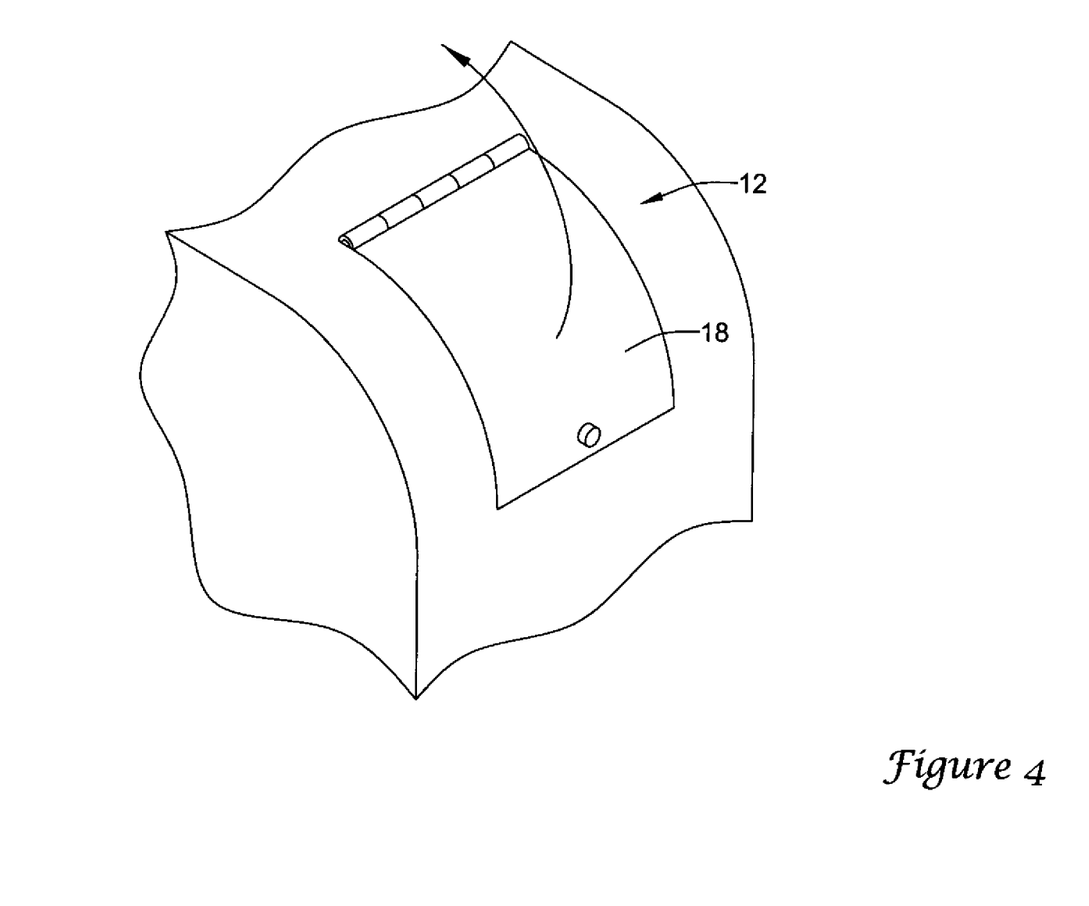
FIG. 4 is a detail including an input aperture useful in the multifunctional sharps container of either FIGS. 1A,B or 2A,B.
Figure 5:
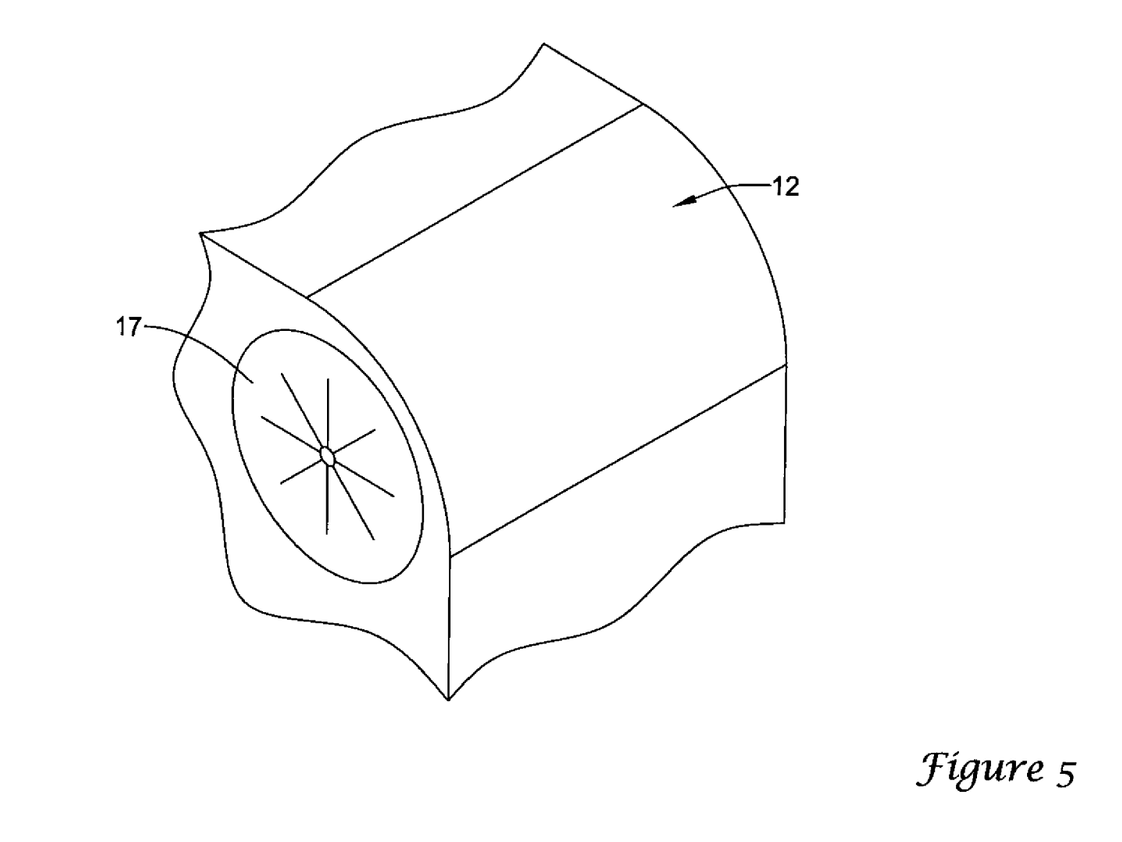
FIG. 5 is a detail including an input aperture useful in the multifunctional sharps container of either FIGS. 1A,B or 2A,B.

FIG. 4 illustrates an alternate input aperture 12 which employs a pivoting hopper 18 to convey a used pen needle or pen needle assembly into compartment 24 of container 10. The hopper opens to accept the pen needle and closes to eject the pen needle into compartment 24. FIG. 5 illustrates an alternate input aperture 12 which employs a flexible diaphragm 17 to convey a pen needle or pen needle assembly into compartment 24 of container 10. These, and other, input aperture structures should function in either a first orientation of the multifunctional container or a second orientation of the multifunctional container. Alternatively, first and second apertures 12 may be provided such that at least one aperture 12 functions in each of the first orientation and the second orientation of the multifunctional container.

Figure 6:
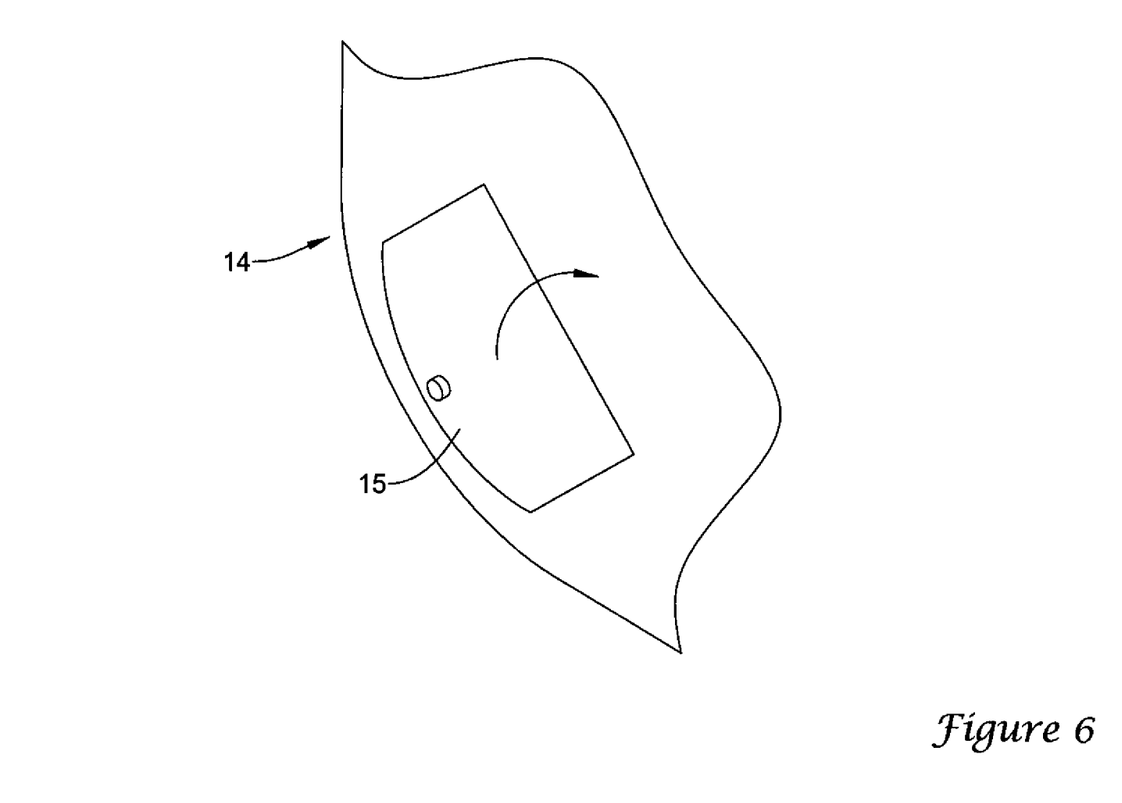
FIG. 6 is a detail including an output aperture useful in the multifunctional sharps container of either FIGS. 1A,B or 2A,B.

FIG. 6 illustrates an output aperture 14 which employs a door 15 allowing one or more pen needles or pen needle assemblies to be removed from compartment 22 of container 10. As may be seen, the corner door 15 provides access to a low portion of compartment 22 in both the vertical and horizontal orientations of FIGS. 1A and 1B or of FIGS. 2A and 2B. The operation of corner door 15 may enhanced by the presence of sloped surface 30 in FIG. 1B which tends to present unused pen needle assemblies near the door under the influence of gravity. In addition to allowing the ready removal of unused pen needle assemblies from compartment 22, door 15 may also allow more than one unused pen needle to be removed at one time, particularly if the pen needles are packaged in groups, for example as a package of two, four, or more. Alternatively, the door may provide access to a series of pen needle assemblies connected to a flexible tape or contained within a cartridge from which a desired number of pen needle assemblies may be removed by the user.

Figure 7:
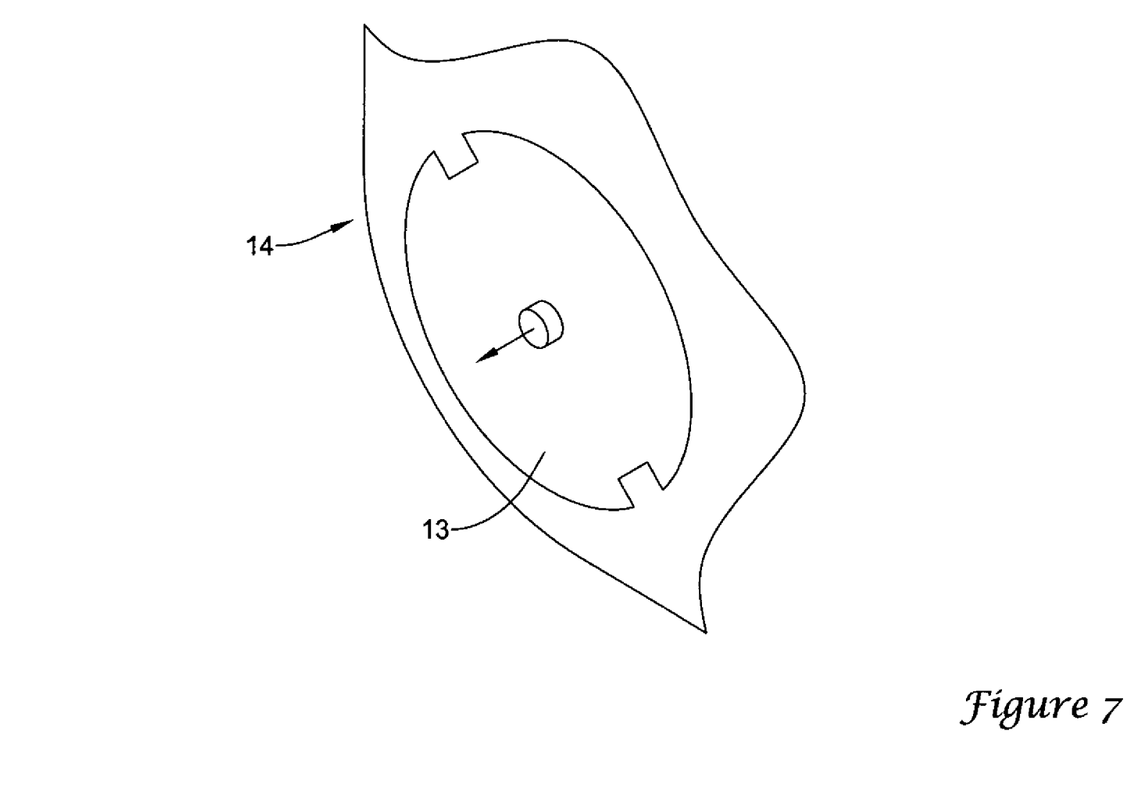
FIG. 7 is a detail including an output aperture useful in the multifunctional sharps container of either FIGS. 1A,B or 2A,B.

FIG. 7 illustrates an output aperture 14 which employs a drawer 13 allowing one or more pen needles or pen needle assemblies to be removed from compartment 22 of container 10. As in the case of door 15, drawer 13 provides access to a lower portion of compartment 22 in both the vertical and horizontal orientations of FIGS. 1A and 1B or of FIGS. 2A and 2B. The operation of drawer 13 may enhanced by the presence of sloped surface 30 in FIG. 1B which tends to present unused pen needle assemblies near the door. Drawer 13 may have low or absent sides to further ensure that at least one of the remaining unused pen needle assemblies lies within the drawer when it is closed. Various internal baffles may be introduced to further direct unused pen needle assemblies into the drawer under the influence of gravity or other forces which may be supplied. As in the case of input aperture structures, these and other, output aperture structures should function in either a first orientation of the multifunctional container or a second orientation of the multifunctional container. Alternatively, first and second apertures 14 may be provided such that at least one aperture 14 functions in each of the first orientation and the second orientation of the multifunctional container. Also as in the case of input aperture structures 12, other forms of output aperture structures, or combinations of output aperture structures, may be employed and the selection of a particular structure for use with a particular type of sharp and container configuration is believed to lie within the ordinary skill of one familiar with the art.

A liquid impermeable partition separates the first compartment from the second compartment within the container. The liquid permeable partition may be rigid or flexible. The perimeter is fixed and sealed to the compartment walls, or other structures which may be present within the container, in a manner which prevents liquid transfer between the first compartment and the second compartment. In some embodiments, the container includes a partition separating the internal storage space from a storage space for unused pen needles, pen needle assemblies, syringe needles, syringe needle covers, and combinations thereof which may flex or otherwise deform from a first position to a second position rather than being rigid. In such embodiments, the volumetric ratio between the internal storage space and the unused pen needle or syringe needle storage space may adjust as the ratio of the volume of used pen needles, pen needle assemblies, syringe needles, syringe needle covers, and combinations thereof to the volume of unused pen needles or syringe needles changes. The change in volumetric ratio within the container may be continuous or discrete. It may occur automatically or may be adjusted manually. Although the liquid impermeable partition is fixed to the container along the entire perimeter of the partition, when the partition is flexible, the partition may have a first position in which the first compartment has a greater volume than the second compartment and a second position in which the second compartment has a greater volume than the first compartment. In such embodiments, the flexible liquid impermeable partition is adapted to move from the first position to the second position and may do so in response to a transfer of sharps from the first compartment to the second compartment. This latter arrangement provides a multifunctional container which utilizes space more efficiently during distribution and use of the container by minimizing unused space within the container throughout its useful lifetime. When all of the unused sharps are present within the first compartment, relatively little unused space is present within the second compartment. Conversely, when most or all of the unused sharps have been removed from the first compartment and transferred to the second compartment, relatively little unused space remains in the first compartment.

In other embodiments, the container includes a means for indicating the fraction of the available internal storage space that is currently occupied by used unused pen needles, pen needle assemblies, syringe needles, syringe needle covers, and combinations thereof. The indicating means may be provided in any convenient way. For example, a translucent case would allow the level of visually contrasting used sharps within the internal storage space to be seen to a sufficient degree. Other options may include counters and moving strip indicators.

In some embodiments, one or both compartments may include a material capable of absorbing and storing fluid associated with the container. The material may be selected from organic or inorganic absorbing materials. Any of the known of fluid absorbing materials and forms may be used providing they have sufficient capacity to hold liquids which may incidentally be introduced into the container along with the sharps to be stored. The following group of materials is intended to be illustrative and non-limiting. Powders of desiccants such as silica gel, calcium sulfate, calcium chloride, montmorillonite clay, and molecular sieves or organic materials such as polyacrylic acid, polymethacrylic acid, polyacrylamide, and polyalkylene oxide may be provided alone or in layered constructions with a liquid permeable sheet. The polymers may conveniently be provided as non-woven pads or as powders. In addition to homopolymers such as those listed, the fluid absorbing material may be copolymers and/or optionally may be crosslinked. The absorbent material may be associated with one or more of the floor and/or walls of the internal storage space. In certain embodiments, the fluid absorbent material within the container has a fluid capacity of at least 0.002 gram for each pen needle or syringe needle to be stored. In other embodiments, the fluid absorbent material within the container has a fluid capacity of at least 0.005 gram or even 0.01 gram for each pen needle or syringe needle to be stored. In yet other embodiments, the available fluid capacity per pen needle or syringe needle may be reduced based upon assumptions regarding the rate of evaporation of fluids from the container and the rate at which additional pen needles or syringe needles are added to the container so long as sufficient capacity is present to absorb the fluid associated with each new pen needle or syringe needle deposited. In those embodiments in which the container includes a liquid absorbing material, the partition may not necessarily be strictly liquid impermeable provided that the liquid absorbent material has sufficient capacity and is situated to intercept any liquid which has been introduced before it can traverse the partition in significant volume.

The first compartment of the multifunctional container is provided with an aperture which allows the removal of one or more unused sharps from the first compartment. The aperture may take any of the forms commonly employed for that purpose. For example, the aperture may comprise a simple opening with a door. Alternatively, it may include a sliding or rotary drawer-like structure which conveys a sharp from the first compartment to the exterior of the multifunctional container. In some embodiments, the sharps are conveyed to a position within the first compartment which adjacent to the aperture by the action of gravity upon the sharps. A multifunctional container employing a gravity feed system conveniently may have two or more functional orientations in which the first dispensing aperture and second receiving aperture are both functional in each functional orientation with the dispensing first aperture being lower than the second receiving aperture. Such gravity feed embodiments may also be facilitated by arranging that the liquid impermeable partition is higher proximate the second aperture and lower proximate the first aperture in each functional orientation. In such gravity feed embodiments, it may be useful to provide a lower internal surface which presents a downward slope leading toward the aperture in at least one functional orientation of the multifunctional container. The internal surface may be an exterior wall of the container or it may be a separate internal structure. In other embodiments, a positive force may be provided to urge the sharps toward an aperture of the first compartment in more than one orientation. In yet other embodiments, the first compartment of the multifunctional container may include unused sharps associated with a roll, reel, stack, serpentine ribbon, or the like which components convey the sharps sequentially to the aperture.

The aperture associated with the first compartment may be configured to facilitate removal of a single unused sharp or it may be configured to facilitate removal of multiple sharps. For example, the sharps may be removed in individual containers such as pen needle assemblies, covered hypodermic needles, covered unibody syringes, or the like. Alternatively, the sharps may be removed as prepackaged multiple sharps, for example, a package of two pen needle assemblies. In some embodiments, the sharps may be presented at the aperture in the form of a continuous strip of packaged sharps from which the user may selectably remove one or more sharps as desired. As indicated above, the aperture and any mechanisms associated therewith, such as doors or drawers, should be operable in any of the functional orientations of the multifunctional container. Alternatively, the multifunctional container may be provided with at least one aperture for removing sharps from the first compartment which is accessible and functional in each of the functional orientations of the multifunctional container.

In some of those embodiments, the storage for unused pen needles or needles may be accessed by a door having a first position and a second position, wherein the structure of the door renders it stable in either the first position or a second position. A suitable door may be formed by providing an anchoring segment and a door segment joined along a line. The line may function as a living hinge and may be a thinned section between the door segment and the anchoring segment. In the first position, the door and the anchoring segment form a generally continuous panel which is convex outward. In one embodiment, the join line is generally perpendicular to a line which bisects the door and is slightly arched with respect to that line. The stiffness of the material from which the door and the anchoring segment are formed as well as the curvature tend to maintain the door in a first position in which the door and anchoring segment form a single curved surface. As the door is opened, the join line buckles and the door and anchoring segment assume a second position in which the door is planar or even somewhat convex in the immediate vicinity of the join line which tends to hold the door in a stable open position. In certain embodiments, container includes dispensing means for unused pen needles or syringe needles.

In some embodiments, the multifunctional container may also have one or more one-way mechanisms, associated with the second aperture, which are capable of conveying one or more of pen needles, hypodermic needles, and syringes with attached hypodermic needles from the exterior of the multifunctional container to the interior of the second compartment. A second aperture may be located at least partially in the upper surface of the multifunctional container in at least one of the functional orientations. In addition, or in the alternative, a second aperture is located at least partially in a lateral surface of the multifunctional container in at least one of the functional orientations. In some embodiments, the one-way mechanism associated with the second aperture is configured to accept and facilitate the removal of a hypodermic needle from one of an associated syringe and an injection pen, further wherein the removed hypodermic needle is conveyed directly into the second compartment. The one-way mechanism associated with the second aperture may be a rotating mechanism, a pivoting mechanism, or a sliding mechanism as are known in the art. Such mechanisms may be provided with color differentiation and/or funnel-like features to guide the user in placing the sharp within the mechanism. Such mechanisms may also include one or more structures which interact with a pen needle, hypodermic needle, or other sharp to facilitate the removal of the sharp from a device to which it is attached prior to disposal. In some embodiments, the one-way mechanism may be a simple flexible diaphragm with a suitable opening or openings. In such embodiments, it maybe desirable to provide a further guard to prevent a sharp within the second container from protruding through the diaphragm. In yet other embodiments, the one-way mechanism associated with the second aperture comprises a device which bends and/or blunts the sharp as it is conveyed from the exterior of the multifunctional container to the interior of the second compartment. In certain embodiments, the one-way mechanism for conveying a used sharp from the exterior of the multifunctional container to the interior of the second compartment is configured to accept both sharps with a protective sheath in place and sharps which have no protective sheath.

In some embodiments, the means for receiving pen needles, pen needle assemblies, syringe needles, syringe needle covers, and combinations thereof is generally frustoconical as seen from the exterior of the container. In this context, "frustoconical" should be broadly interpreted to include frusta of cones having bases other than circles. The bases may be, for example, ellipses, regular or irregular polygons or other closed curves. In some embodiments, the lateral surface of the cone may be described as formed by straight line segments moving along the base, however in other embodiments, the surface may be formed by moderately curved lines. The cone may be a right cone or may be an oblique cone. Generally it is believed that the walls of the cone should form approximately a 45 degree angle with the axis of an inserted pen needle or syringe to provide both a broad entry aperture and a good degree of guidance for the insertion of the pen needle or syringe needle into the device. In some embodiments, the frustoconical receiving portion of the disposal container may smoothly join a similar frustoconical portion of the housing when the receiving portion is positioned to receive a pen needle, pen needle assembly, syringe needle, syringe needle cover, or combinations thereof in at least one position of the frustoconical portion relative to the housing.

Particularly in those embodiments in which a pen needle assembly or syringe needle cover is to be inserted axially into the frustoconical receiving portion of the container, it is generally desirable that the frustoconical portion have a height sufficient to contain a pen needle assembly or syringe needle cover within the frustoconical portion. This height will often be greater than the height necessary to contain only a pen needle or syringe needle and may be seen as allowing the receiving portion to rotate to a position within the container without undue interference with the surrounding housing.

In some embodiments, the portion of the container which receives pen needles, pen needle assemblies, syringe needles, syringe needle covers, and combinations thereof provides a visual contrast to the surrounding portions of the housing to aid visually impaired users in properly orienting and inserting the pen needles, pen needle assemblies, syringe needles, syringe needle covers, and combinations thereof. The visual distinctive feature may be provided in the form of color contrast and/or patterning relative to the surrounding housing. Preferably, the color associated with the receiving region or a patterned portion thereof will be red.

In some embodiments, the means for receiving pen needles includes a combination of protrusions and recesses which engage the pen needle to prevent rotation thereof as a pen is rotated relative to the pen needle within the said means. This engagement facilitates one hand removal of a pen needle from a medical delivery pen, thereby minimizing the risk of accidental sticks.

In some embodiments, the means for receiving pen needles, pen needle assemblies, syringe needles, syringe needle covers, and combinations thereof includes a means for rotating the receiving means relative to the housing. In certain embodiments, the rotation will be about an axis generally perpendicular to an axis associated with the pen needle, pen needle assembly, syringe needle, syringe needle cover, or combinations thereof which are to be conveyed into the interior storage space. In other embodiments, the rotation will be about an axis which is generally parallel to an axis associated with the pen needle, pen needle assembly, syringe needle, syringe needle cover, or combinations thereof which are to be conveyed into the interior storage space. The means for rotating the receiving means may be either manual or automated as by a spring drive or electric motor.

In some embodiments, the means for receiving pen needles, pen needle assemblies, syringe needles, syringe needle covers, and combinations thereof includes an ejector assembly having an ejector axis and wherein the means for receiving pen needles, pen needle assemblies, syringe needles, syringe needle covers, and combinations thereof is operatively coupled to the means for rotating said receiving means relative to the housing. In those embodiments, it is preferred that rotation of the receiving means convey the pen needles, pen needle assemblies, syringe needles, syringe needle covers, and combinations thereof within the internal storage space whereupon the ejector assembly ejects the pen needle, pen needle assembly, syringe needle, syringe needle cover, or combinations thereof from the receiving means into the internal storage space.

In some embodiments, the container includes one or more guards which prevent pen needles, pen needle assemblies, syringe needles, syringe needle covers, or combinations thereof within the internal storage space from re-entering the means for receiving and ejecting pen needles, pen needle assemblies, syringe needles, syringe needle covers, and combinations thereof This is desirable to prevent accidental or intentional removal of sharps from the internal storage space, particularly when the container is inverted or otherwise placed in an orientation other than that normally employed for dispensing and disposing of sharps. Absent such guards, sharps might accidentally be released during transport. In certain embodiments, the one or more guards are structures within the internal storage space which prevent access to the receiving means in positions other than those associated with receiving or ejecting pen needles, pen needle assemblies, and combinations thereof Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed is:

1. A multifunctional container for safe storage of medical or laboratory sharps comprising:
    a first compartment and a second compartment and a flexible liquid impermeable partition therebetween,
    wherein said flexible liquid impermeable partition is sealed to the multifunctional container along an entire perimeter of the flexible liquid impermeable partition in a manner which prevents liquid transfer between the first compartment and the second compartment;
    said first compartment defines an internal storage space sized and configured to contain an initial quantity of one or more unused sharps, said initial quantity of one or more unused sharps selected from pen needles, hypodermic needles, and syringes with attached hypodermic needles being present within the first compartment at a first time,
    wherein the first compartment further comprises a first aperture which may be opened to remove one or more unused sharp; and
    said second compartment sized and configured to contain a quantity of used sharps substantially equal to the initial quantity of one or more unused sharps at a second time, said one or more used sharps selected from pen needles, hypodermic needles, and syringes with attached hypodermic needles,
    wherein the second compartment further comprises a second aperture which has associated therewith a one-way mechanism configured and adapted to convey a used sharp from the exterior of the multifunctional container irreversibly into the interior of the second compartment,
    wherein the flexible liquid impermeable partition is configured and adapted to flex or deform from a first position to a second position such that a volumetric ratio between the internal storage space and the unused pen needle or syringe needle storage space may adjust as the ratio of the volume of contained used sharps to the volume of contained unused sharps changes.

2. The multifunctional container of claim 1, wherein the combined volumes of the first compartment and second compartment are at all times capable of containing the initial quantity of one or more unused sharps.

3. The multifunctional container of claim 2, wherein a portion of the flexible liquid impermeable partition is adapted to move from the first position to the second position in response to a transfer of sharps from the first compartment to the second compartment.

4. The multifunctional container of claim 1, wherein the first aperture of the first compartment allows removal of one unused sharp of the initial quantity of one or more unused sharps from the first compartment.

5. The multifunctional container of claim 1, wherein the first aperture of the first compartment allows removal of more than one unused sharp of the initial quantity of one or more unused sharps from the first compartment.

6. The multifunctional container of claim 5, wherein the first aperture of the first compartment allows removal of more than one unused sharp of the initial quantity of one or more unused sharps from the first compartment, said more than one unused sharps being packaged as a single unit.

7. The multifunctional container of claim 1, wherein the multifunctional container has two or more orientations in which the first aperture and second aperture are each functional for their recited function such that in each functional orientation of the two or more orientations, the first aperture is lower than the second aperture.

8. The multifunctional container of claim 7, wherein a first portion of the flexible liquid impermeable partition is higher proximate the second aperture and a second portion of the flexible liquid impermeable partition is lower proximate the first aperture in each functional orientation of the two or more orientations.

9. The multifunctional container of claim 7, wherein the second aperture is located at least partially in an uppermost surface of the multifunctional container in at least one of the two or more functional orientations of the two or more orientations.

10. The multifunctional container of claim 7, wherein the second aperture is located at least partially in a lateral surface of the multifunctional container in at least one of the two or more functional orientations of the two or more orientations.

11. The multifunctional container of claim 1, wherein the one-way mechanism associated with the second aperture is configured to accept and facilitate removal of a hypodermic needle from one of an associated syringe and an injection pen.

12. The multifunctional container of claim 1, wherein the one-way mechanism associated with the second aperture is a rotating mechanism.

13. The multifunctional container of claim 1, wherein the one-way mechanism associated with the second aperture is a pivoting mechanism.

14. The multifunctional container of claim 1, wherein the one-way mechanism associated with the second aperture includes a sliding component.

15. The multifunctional container of claim 1, wherein the one-way mechanism is configured to accept both used and unused sharps with a protective sheath in place and used and unused sharps which have no protective sheath.

16. The multifunctional container of claim 1, wherein said second compartment further comprises a liquid absorbent material having a liquid capacity of at least 0.002 gram per contained used sharp, the used sharp selected from pen needles, hypodermic needles, and syringes with attached hypodermic needles.

17. The multifunctional container of claim 1, wherein said second compartment further comprises a liquid absorbent material having a liquid capacity of at least 0.005 gram per contained used sharp, the used sharp selected from pen needles, hypodermic needles, and syringes with attached hypodermic needles.

18. The multifunctional container of claim 1, wherein said second compartment further comprises a liquid absorbent material having a liquid capacity of at least 0.01 gram per contained used sharp, the used sharp selected from pen needles, hypodermic needles, and syringes with attached hypodermic needles.

19. The multifunctional container of claim 1, wherein the flexible liquid impermeable partition is elastic and may deform under pressure.

20. The multifunctional container of claim 1, wherein the flexible liquid impermeable partition is provided with sufficient extra material to allow it to deflect between the first position in which the first compartment has a greater volume than the second compartment and the second position in which the second compartment has a greater volume than the first compartment.

* * * * *